United States Patent
Loeliger

(10) Patent No.: US 6,316,453 B1
(45) Date of Patent: Nov. 13, 2001

(54) AQUEOUS PHARMACEUTICAL COMPOSITION

(75) Inventor: Peter Loeliger, Muttenz (CH)

(73) Assignee: Actelion Pharmaceuticals Ltd. (CH)

( * ) Notice: Subject to any disclaimer, the term of this patent is extended or adjusted under 35 U.S.C. 154(b) by 0 days.

(21) Appl. No.: 09/573,504

(22) Filed: May 18, 2000

(51) Int. Cl.[7] .............................. A01N 43/54; A61K 9/08; A61K 31/513; A61K 47/18

(52) U.S. Cl. ........................................... 514/256; 514/970

(58) Field of Search ...................................... 514/256, 970

(56) References Cited

U.S. PATENT DOCUMENTS 6,004,965 * 12/1999 Breu et al. ........................... 514/256

* cited by examiner

*Primary Examiner*—Frederick Krass
(74) *Attorney, Agent, or Firm*—Pennie & Edmonds LLP

(57) ABSTRACT

Difficulties in preparing a stable pharmaceutical composition containing 5-Isopropyl-pyridine-2-sulfonic acid 6-(2-hydroxy-ethoxy)-5(2-methoxy-phenoxy)2-(2-1H-tetrazol-5-yl-pyridin-4yl)-pyrimidin-4-ylamide in form of the water soluble disodium salt, a buffer and preferably a metal complex forming agent, have been encountered. It was unexpectedly found that these difficulties can be overcome by adjusting the pH of the solution with an acid to over and above 8,2, preferably to 9,0, but not higher than 10.

12 Claims, No Drawings

AQUEOUS PHARMACEUTICAL COMPOSITION

The invention relates to a stable aqueous pharmaceutical composition comprising containing 5-isopropyl-pyridine-2-sulfonic acid 6-(2-hydroxy-ethoxy)-5(2-methoxy-phenoxy) 2-(2-1H-tetrazol-5-yl-pyridin-4yl)-pyrimidin-4-ylamide in form of the water soluble disodium salt, a buffer and a metal complex forming agent, the liquid having a pH of over and above 8.2 but not higher than 10.

Some of the salts of 5-isopropyl-pyridine-2-sulfonic acid 6-(2-hydroxy-ethoxy)-5(2-methoxy-phenoxy)2-(2-1H-tetrazol-5-yl-pyridin-4yl)-pyrimidin-4-ylamide are water soluble and the preparation of an aqueous pharmaceutical composition containing the disodium salt appeared to be without any problems.

Vials for clinical testing of 5-isopropyl-pyridine-2-sulfonic acid 6-(2-hydroxy-ethoxy)-5(2-methoxy-phenoxy) 2-(2-1H-tetrazol-5-yl-pyridin-4yl)-pyrimidin-4-ylamide have been prepared by dissolving the compound in water containing as buffer 2-amino-2-hydroxymethyl-1,3-propandiol and very small amounts of ethylene diaminetetraacetic acid disodium salt as a competitive metal complex forming agent and thereafter heating the mixture in an autoclave for 20 minutes at about 121° C. in order to sterilize the mixture in the vials (compare General Example which can be considered to correspond to a usual way of preparing such a water soluble formulation).

After storage of the vials at room temperature for about a year the inspection thereof revealed that the liquid contains in a number of vials visual particles which is not the case in a stable pharmaceutical composition. The number of such undesired visual particles increased with time of storage. This fact rendered these vials unsuitable for clinical trials and commercial purposes because already after some months of storage particles were visible and hence the storage time and consequently the expiration date of a given batch was much too short.

Since for practical purposes it is not feasible to run real time experiments with different parameters like different buffers, different metal complex forming agents, different origins of the ingredients, different filter media, different stopper types, different glass types of the vials, different sterilizing times etc. because for each such experiment the results would only be available after at least a year of storage, a model experiment was therefore developed in form of stress heating the vials. The assumption was made that after prolonged heating at 121° C. a simulation of a long storage time is achieved. It was further expected that the results obtained after cooling of the vials to room temperature will correspond to the results of a storage time of at least one year i.e. formation of small visual particles will occur. However, even with up to 12 hours of stress heating at 121° C. no particles could be seen after cooling the vials to room temperature. Even after hours and/or days the solution in the vials was still clear.

It happened that in a repetition of stress experiments vials were used from a batch presumably prepared identical to the vials from the batch used in an earlier experiments. However this batch behaved differently inasmuch as after 12 hours of heating at 121° C. a precipitate formed after cooling to room temperature. Direct comparison of the two batches confirmed the different behaviour.

By means of HPLC it could be shown that this precipitate consisted mainly of a single substance (single HPLC-peak) which is called hereinafter compound X. Beside compound X a number of other completely soluble decomposition products in more or less similar amounts as compound X can be detected in the HPLC chromatogram.

Careful examination of the two batches revealed that in the batch with the precipitate the pH by mistake had been adjusted to 7.58 instead to 8.0. Therefore the investigation of the influence of the pH on precipitate formation in a number of stress heating experiments was now performed. It was found that the formation of compound X and the other decomposition products was depending on the pH of the formulation and this formation was very small—if at all—at a pH over and above pH 8.2. For further verification and demonstration stress heating experiments were performed in a time range up to 64 hours. In the following Table 1 the results of representative experiments (which are described in detail in the experimental part) are outlined:

TABLE 1

| Experiment | pH | Stress heating time (121° C.) | % Educt found | % Compound X found |
|---|---|---|---|---|
| 1 | 7.0 | 12 hrs | 96.02 | 1.00 |
| 2 | 8.0 | 12 hrs | 98.06 | 0.38 |
| 3 | 8.5 | 12 hrs | 98.63 | 0.20 |
| 4 | 9.0 | 12 hrs | 98.93 | 0.12 |
| 5 | 7.0 | 64 hrs | 78.62 | 4.99 |
| 6 | 8.0 | 63 hrs | 98.06 | 1.17 |
| 7 | 8.5 | 63 hrs | 98.24 | 0.45 |
| 8 | 9.0 | 63 hrs | 98.76 | 0.21 |

In addition to the figures outlined in Table 1 it may be stated that the content of Educt and Compound X after 20 min. of sterilizing the vials at 121° C. i.e. under "normal sterilization conditions" but applying the pH- conditions given in Table 1 were 99.30% to 99.33% Educt 0.08% to 0.09% Compound X.

The results set forth in Table 1 illustrate that the increase of the formation of Compound X after 12 hrs at 121° C. in the pH 9 formulation as compared to the "normal sterilization conditions" is almost negligible, i.e. 0.03%, whereas e.g. at pH 8 the increase is 10 times higher, i.e. 0.3%.

It could further be shown, by filtering a large number of vials originally prepared ("normal sterilization conditions") and stored longer than one year at room temperature and investigating the tiny amounts of particles (residue) sitting on the filter by dissolving them with Ethanol in order to perform HPLC analysis, that these particles did also contain as a major component compound X.

This fact is not understood since compound X is rather readily water soluble. However this finding allows the conclusion that—although even after 12 hours of stress heating at pH 8.0 a clear solution is obtained—a normal formulation prepared without stress heating can form such very small but sometimes visible particles (maybe together with another carrier?) after a long time (several months) of storage at room temperature. This, in spite of the fact that the main component of the particles is compound X which is readily water soluble.

These findings allowed to conceive a drastically improved and stable pharmaceutical composition which is assumed to be and to remain free of visible particle. This assumption turned out to be so far correct even after 14 months of storage at room temperature.

Therefore, the invention relates to a stable aqueous pharmaceutical composition (not forming visible particles on storage) comprising containing 5-isopropyl-pyridine-2-sulfonic acid 6-(2-hydroxy-ethoxy)-5(2-methoxy-phenoxy) 2-(2-1H-tetrazol-5-yl-pyridin-4yl)-pyrimidin-4-ylamide in form of the water soluble disodium salt, a buffer and, preferably, a metal complex forming agent, the liquid having a pH of over and above 8.2 but not higher than 10.

Furthermore the invention relates to a process for the preparation of a stable aqueous pharmaceutical composition (not forming visible particles on storage) comprising dissolving 5-isopropyl-pyridine-2-sulfonic acid 6-(2-hydroxy-ethoxy)-5(2-methoxy-phenoxy)2-(2-1H-tetrazol-5-yl-pyridin-4yl)-pyrimidin-4-ylamide in form of the water soluble disodium salt in water, adding to the solution a buffer, preferably a metal complex forming agent and titrating the mixture obtained with an acid until a pH over and above 8.2 but not higher than 10 is reached.

A preferred acid for adjusting the pH of the mixture is 2 N hydrochloric acid. A preferred range of the pH is between 8.5 and 9.5. The preferred pH is 9.

A preferred buffer is 2-amino-2-hydroxymethyl-1,3-propanediol (TRIS) and a preferred metal complex forming agent is ethylene diaminetetraacetic acid disodium salt (EDTA). A preferred mixture consists of 0.01 to 0.1% EDTA and 0.1 to 1.0% of TRIS.

EXPERIMENTAL PART

The following experiments describe in detail how the results set forth in experiments 1 to 8 in Table 1 have been obtained. The experiments are illustrating the invention but do not limit the scope thereof.

General Experiment illustrating the Preparation of Formulations

1. In a glass or stainless steel container place a volume of Nitrogen-gassed water for injection equal to approximately 90% of the final volume to be manufactured (according to the following amounts specified for about 1 liter).
2. Add and dissolve the following excipients in the water while mixing:
   1.21 g 2-Amino-2-hydroxymethyl-1,3-propanediol (TRIS)
   0.1 g Ethylene diaminetetraacetic acid disodium salt (EDTA)
   7.2 g Sodium chloride
3. With strong mixing, slowly add 26.81 g of 5-Isopropyl-pyricline-2-sulfonic acid 6-(2-hydroxy-ethoxy)-5(2-methoxy-phenoxy)2-(2-1H-tetrazol-5-yl-pyridin-4yl)-pyrimidin-4-ylamide disodium salt by stewing it on the water surface. The formation of clots of substance is avoided.
4. Check and record the pH of the solution. Adjust to the desired pH with freshly prepared 2 N Hydrochloric Acid Solution.
5. Bring the solution to the final 1.0 liter volume with water for injection and mix thoroughly. Check and record the final pH of the solution (as desired).
6. Sterilize solution by filtration through a sterile 0.2 um-rated filter into a sterile receiving flask.
7. Aseptically fill the solution into clean, sterile, depyrogenated glass vials and insert a sterile serum stopper onto each vial.
8. Seal the stopper with a cap.
9. Sterilize the filled and closed vials in a circulating water autoclave 20 min. at 121° C.

Experiment 1

The General Example is repeated using the adjustments of pH and stress heating time as set forth in Table 1, i.e.
pH 7; stress heating time (at 121° C.) 12 hours.

Experiment 2

The General Example is repeated using the adjustments of pH and stress heating time as set forth in Table 1, i.e.
pH 8; stress heating time (at 121° C.) 12 hours.

Experiment 3

The General Example is repeated using the adjustments of pH and stress heating time as set forth in Table 1, i.e.
pH 8.5; stress heating time (at 121° C.) 12 hours.

Experiment 4

The General Example is repeated using the adjustments of pH and stress heating time as set forth in Table 1, i.e.
pH 9; stress heating time (at 121° C.) 12 hours.

Experiment 5

The General Example is repeated using the adjustments of pH and stress heating time as set forth in Table 1, i.e.
pH 7; stress heating time (at 121° C.) 64 hours.

Experiment 6

The General Example is repeated using the adjustments of pH and stress heating time as set forth in Table 1, i.e.
pH 8; stress heating time (at 121° C.) 63 hours.

Experiment 7

The General Example is repeated using the adjustments of pH and stress heating time as set forth in Table 1, i.e.
pH 8.5; stress heating time (at 121° C.) 63 hours.

Experiment 8

The General Example is repeated using the adjustments of pH and stress heating time as set forth in Table 1, i.e.
pH 9; stress heating time (at 121° C.) 63 hours.
Result:
The formulations illustrated by Experiments 1, 2, 5 and 6 when performed without stress heating do form visible particles after storage of several months at room temperature.

The formulations illustrated by experiments 3, 4, 7 and 8 when performed without stress heating do not form visible particles after storage of several months at room temperature.

What is claimed is:
1. A stable aqueous pharmaceutical composition comprising 5-isopropyl-pyridine-2-sulfonic acid 6-(2-hydroxy-ethoxy)-5(2-methoxy-phenoxy)2-(2-1H-tetrazol-5-yl-pyridin-4yl)-pyrimidin-4-ylamide in form of a water soluble disodium salt and a buffer, the composition having a pH of 8.2 but not higher than 10.
2. The stable aqueous pharmaceutical composition according to claim 1, further comprising a metal complex forming agent.
3. The stable aqueous pharmaceutical composition according to claim 2, further comprising as metal complex forming agent, ethylene diaminetetraacetic acid disodium salt.

4. The stable aqueous pharmaceutical composition according to claim 1, further comprising as buffer, 2-amino-2-hydroxymethyl-1,3-propanediol.

5. The stable aqueous pharmaceutical composition according to claim 1, further comprising a mixture of 2-amino-2-hydroxymethyl-1,3-propanediol and ethylene diaminetetraacetic acid disodium.

6. The stable aqueous pharmaceutical composition according to claim 1, further comprising a mixture of 0.1 to 1.0% 2-amino-2-hydroxymethyl-1,3-propanediol and 0.01 to 0.1% ethylene diamine tetraacetic acid disodium.

7. The stable aqueous pharmaceutical composition according to claim 1, wherein the pH is in between 8.5 and 9.5.

8. The stable aqueous pharmaceutical composition according to claim 1, wherein the pH is 9.0.

9. A process for preparation of a stable aqueous pharmaceutical composition comprising the steps of:

dissolving 5-isopropyl-pyridine-2-sulfonic acid 6-(2-hydroxy-ethoxy)-5(2-methoxy-phenoxy)2-(2-1H-tetrazol-5-yl-pyridin-4yl)-pyrimidin-4-ylamide in the form of a water soluble disodium salt in water to obtain a solution, adding to the solution a buffer to obtain a mixture and titrating the mixture with an acid until the pH of the mixture reaches 8.2 or higher but not higher than 10.

10. The process according to claim 9, further comprising adding to the mixture a metal complex forming agent.

11. The process according to claim 9, wherein titrating is conducted with 2N hydrochloric acid until a pH of 9.0 is reached.

12. A method comprising administering a stable aqueous pharmaceutical composition according to claim 1 to a human.

* * * * *